United States Patent [19]

Brahm et al.

[11] Patent Number: 5,672,736
[45] Date of Patent: Sep. 30, 1997

[54] POLYISOCYANATES CONTAINING ALLOPHANATE GROUPS

[75] Inventors: Martin Brahm, Engelskirchen; Lutz Schmalstieg; Josef Pedain, both of Köln, all of Germany

[73] Assignee: Bayer Aktiengesellschaft, Leverkusen, Germany

[21] Appl. No.: 555,200

[22] Filed: Nov. 8, 1995

[30] Foreign Application Priority Data

Nov. 18, 1994 [DE] Germany .................. 44 41 176.6

[51] Int. Cl.$^6$ .................................................. C07C 263/00
[52] U.S. Cl. .................... 560/345; 560/330; 528/49; 528/59; 528/67; 252/182.2
[58] Field of Search ................................ 560/345, 330; 528/49, 59, 67; 252/182.2

[56] References Cited

U.S. PATENT DOCUMENTS

| 3,769,318 | 10/1973 | Windemuth et al. | 260/471 C |
| 4,160,080 | 7/1979 | König et al. | 528/59 |
| 4,810,820 | 3/1989 | Slack et al. | 560/27 |
| 5,319,054 | 6/1994 | Slack et al. | 528/48 |
| 5,606,001 | 2/1997 | Shaffer | 528/49 |

FOREIGN PATENT DOCUMENTS 994890  6/1965  United Kingdom .

Primary Examiner—Samuel Barts
Attorney, Agent, or Firm—Joseph C. Gil; Thomas W. Roy

[57] ABSTRACT

The present invention relates to a process for preparing polyisocyanates containing allophanate groups by reacting compounds a), which i) contain urethane groups, but which are substantially free of hydroxyl groups and isocyanate groups, ii) have an average of at least two urethane groups per molecule, iii) are prepared by reacting organic isocyanates a1) with organic hydroxyl compounds a2) and iv) have an average molecular weight of at most 2,500, with excess quantities, based on the urethane groups, of distillable organic polyisocyanates b) to form polyisocyanates containing allophanate groups and subsequently removing by distillation the unreacted excess of component b) to a residual content of less than 0.5 wt. %, provided that polyisocyanates a1) and polyisocyanates b) are different.

The present invention also relates to the products obtained from this process and to their use as binders or binder components in coating compositions.

21 Claims, No Drawings

POLYISOCYANATES CONTAINING ALLOPHANATE GROUPS

BACKGROUND OF THE INVENTION

1. Field of the Invention

The present invention relates to a process for preparing polyisocyanates containing allophanate groups, the polyisocyanates obtained by this process and their use as binders or binder components in coating compositions.

2. Description of the Prior Art

Polyisocyanates containing allophanate groups and their use in binders are known (cf. for example GB-PS 994,890, EP-A-0,000,194 or EP-A-0,303,150). The preparation of these polyisocyanates is generally carried out by reacting excess quantities of mostly aliphatic or cycloaliphatic diisocyanates with monohydric or polyhydric alcohols. After the urethanization and allophanatization reactions, the excess of volatile isocyanate compounds is removed by distillation and products are formed having properties which can be varied widely according to the diisocyanate used. The preparation of polyisocyanates containing allophanate groups from aromatic diisocyanates is described, for example, in U.S Pat. No. 3,769,318. One of the disadvantages of these aromatic allophanate polyisocyanates is their poor heat stability, such that during thin-film distillation the allophanate polyisocyanates regenerate the incorporated diisocyanates, which renders impossible a complete separation of the excess diisocyanate following the allophanatization reaction.

Accordingly, it is an object of the present invention to provide thermally stable polyisocyanates containing allophanate groups.

This object may be achieved in accordance with the present invention, which is described in more detail below. These polyisocyanates are prepared by using different isocyanate components for the urethanization and the subsequent allophanatization reactions. Because they contain different isocyanate groups in chemically bound form, the resulting polyisocyanates are referred to below as "heteroallophanates." The properties of these heteroallophanates, in particular their viscosity and reactivity, and the properties of the coatings produced from them, such as hardness and elasticity, can easily be controlled by suitable selection of the isocyanate component employed in each of the urethanization and allophanatization reactions. The heat stability of the resulting products is of particular importance when aromatic diisocyanates, in particular diisocyanatotoluene, are used in the allophanatization reaction.

The ability to achieve the above-mentioned variability in the properties of the products and the coatings prepared therefrom by using mixtures of isocyanates, in particular mixtures of diisocyanates, in the urethanization and subsequent allophanatization reactions, is not possible because of the frequently inadequate heat stability of the "mixed allophanate" obtained and because of the disadvantage that the resulting products, unlike those obtained in accordance with the process of the present invention, are polyisocyanates containing isocyanate groups of differing reactivity.

SUMMARY OF THE INVENTION

The present invention relates to a process for preparing polyisocyanates containing allophanate groups by reacting compounds a), which i) contain urethane groups, but which are substantially free of hydroxyl groups and isocyanate groups, ii) have an average of at least two urethane groups per molecule, iii) are prepared by reacting organic isocyanates a1) with organic hydroxyl compounds a2) and iv) have an average molecular weight of at most 2,500, with excess quantities, based on the urethane groups, of distillable organic polyisocyanates b) to form polyisocyanates containing allophanate groups and subsequently removing by distillation the unreacted excess of component b) to a residual content of less than 0.5 wt. %, provided that polyisocyanates a1) and polyisocyanates b) are different.

The present invention also relates to the products obtained from this process and to their use as binders or binder components in coating compositions.

DETAILED DESCRIPTION OF THE INVENTION

Starting materials for the process according to the invention are compounds a) containing urethane groups and organic polyisocyanates b), which are reacted with compounds a) containing urethane groups to form polyisocyanates containing allophanate groups.

Compounds a) containing urethane groups have an average of at least two urethane groups per molecule and a number average molecular weight, which may be calculated from the stoichiometry of the starting materials, of at most 2,500, preferably at most 1,500. Compounds a) are "substantially" free of isocyanate groups and hydroxyl groups, i.e., the NCO content of compounds a) is at most 2 wt. %, preferably at most 0.5 wt. % and more preferably at most 0.2 wt. % and the hydroxyl group content is at most 1 wt. %, preferably at most 0.3 wt. % and more preferably at most 0.1 wt. %. This objective is achieved during the preparation of compounds a) by reacting the starting components a1) and a2) at an NCO/OH equivalent ratio of 1.2:1 to 1:1.2, preferably of 1.1:1 to 1:1.1 and more preferably 1:1. This reaction to form urethane groups is generally carried out at a temperature of 20° to 130° C., preferably 50° to 90° C. The reaction is preferably carried out in the melt.

Isocyanates a1) are selected from (cyclo)aliphatic and/or aromatic mono-, di- and/or polyisocyanates having a molecular weight 99 to 1,000, preferably 140 to 300 and an NCO content of 10 to 56 wt. %, preferably 18 to 56 wt. % and more preferably 30 to 50 wt. %. The average NCO functionality of component a) is 1 to 6, preferably 2 to 3.5 and more preferably 2. Isocyanate component a1) is preferably selected from diisocyanates, in particular linear aliphatic or cyclic diisocyanates. By "cyclic" diisocyanates are meant those which contain at least one aromatic ring or at least one cycloaliphatic ring per molecule.

Examples of monoisocyanates, which can be used as component a1) or as part of component a1), include phenyl isocyanate and (cyclo)aliphatic monoisocyanates having 4 to 18 carbon atoms such as n-butyl isocyanate, cyclohexyl isocyanate or n-stearyl isocyanate.

Examples of suitable diisocyanates include tetramethylene diisocyanate, pentamethylene diisocyanate, hexamethylene diisocyanate (HDI), undecamethylene diisocyanate, dodecamethylene diisocyanate, 1-isocyanato-3,3,5-trimethyl-5-isocyanatomethylcyclohexane (IPDI), 4,4'-bis(isocyanatocyclohexyl)methane and mixtures thereof with the corresponding 2,4'- and optionally 2,2'-isomers (HMDI), 1-methyl-2,4-diisocyanatocyclohexane and mixtures thereof with 1-methyl-2,6-diisocyanatohexane (HTDI), 1-isocyanato-4(3)-isocyanatomethyl-1-methylcyclohexane, p-xylylene diisocyanate and mixtures thereof. Aromatic diisocyanates such as 2,4- and/or 2,6-diisocyanatotoluene (TDI) and 2,4'- and/or 4,4'-diisocyanatodiphenyl-methane (MDI) are also suitable as component a1) or as part of this component.

Derivatives of the above-mentioned isocyanates containing biuret groups, uretdione groups, isocyanurate groups or carbodiimide groups are also suitable in principle as component a1) or as part of this component, but the use of such modification products is not preferred.

Component a1) is preferably selected from HDI, HMDI, IPDI or HTDI.

Alcohol component a2) is selected from monohydric to hexahydric alcohols having a molecular weight 32 to 900, preferably 74 to 300, and any mixtures of such alcohols. Examples of suitable monohydric alcohols include saturated monohydric alcohols such as methanol, ethanol, n-propanol, isopropanol, methoxypropanol and the isomeric butanols, pentanols, hexanols, octanols, decanols, dodecanols and octadecanols. Examples of polyhydric alcohols include ethylene glycol, propylene glycol, butanediol-1,4, hexanediol-1,6, neopentyl glycol, 2-methylpropanediol-1,3, 2,2,4-trimethylpentanediol-1,3, dimeric fatty alcohols, trimeric fatty alcohols, glycerol, trimethylolpropane, trimethylolethane, the isomeric hexanetriols, pentaerythritol and sorbitol. Also suitable are unsaturated alcohols such as allyl alcohol, trimethylolpropane diallyl ether, butenediol and monofunctional alcohols that are derived from corresponding acids or acidic mixtures of unsaturated synthetic and naturally-occurring fatty acids.

Also suitable, but not preferred are alkoxylation products containing ether groups of the monohydric and polyhydric alcohols previously set forth and/or transesterification products containing hydroxyl groups of fats or oils with polyhydric alcohols, in particular glycerol, trimethylolpropane or pentaerythritol.

The molecular weight of component a) is adjusted by suitable selection of starting components a1) and a2) and, in particular, by their average functionality. Since high-molecular compounds are not suitable as component a), at least a portion of component a1) and/or component a2) is made up of monofunctional components to bring about chain termination during the reaction to form urethane. This means that the average functionality of components a1) and a2) is less than 2.

As stated above, component a) is prepared by reacting individual components a1) and a2) to form urethane groups. It is also possible, but not preferred, to use urethane group-containing compounds prepared by other methods such as the known "phosgene-free urethane synthesis" described, for example, in EP-A-0,027,940, EP-A-0,027,952, EP-A-0,027,953, EP-A-0,323,514 and EP-A-0,355,443.

Isocyanate component b) is selected from the distillable organic polyisocyanates previously set forth for component a1) with the exception of 2,2-, 2,4'- and 4,4'-diisocyanato-diphenylmethane, although component b) should contain no monoisocyanates. The average NCO functionality of component b) is 2 to 4, preferably 2, i.e., diisocyanates are preferably used exclusively as component b).

Component b) is preferably selected from TDI, IPDI, HTDI, HMDI or HDI are employed as component b).

A critical feature of the invention is that different isocyanates are used as component a1) and component b). Therefore, when mixtures of isocyanates are used as component a1) and/or component b), at most 10 wt. % of the isocyanates present in the respective components are identical. Preferably, component b) exclusively contains isocyanates which are not present in component a1). In this connection positional isomers of same isocyanates such as 2,4- and 2,6-TDI, 2,4- and 2,6-HTDI, 2,4'-, 2,2'- and 4,4'-MDI, 2,4'-, 2,2'- and 4,4'-HMDI are not regarded as different isocyanates.

Particularly preferred are combinations of HDI as component a1) and TDI as component b), HDI as component a1) and IPDI as component b), HDI as component a1) and HTDI as component b), HMDI as component a1) and HDI as component b), IPDI as component a1) and HDI as component b) and HTDI as component a1) and HDI as component b).

The reaction of urethane component a) with isocyanate component b) is carried out in an NCO/urethane equivalent ratio of 3:1 to 100:1, preferably 6:1 to 60:1 and more preferably 8:1 to 30:1 at a temperature of 40° C. to 150° C., preferably 50° C. to 120° C. and more preferably 60° C. to 90° C. Preferably known catalysts are employed to accelerate the allophanatization reaction. Examples of these catalysts include tetraalkylammonium hydroxides or arylalkylammonium hydroxides; metal salts such as iron(III) chloride or potassium octoate; zinc compounds such as zinc stearate, zinc octoate, zinc naphthenate or zinc acetylacetonate; tin compounds such as tin(II) octoate, tin(II) ethylhexanoate, tin(II) laurate, dibutyltin oxide, dibutyltin dichloride, dibutyltin diacetate, dibutyltin dilaurate, dibutyltin maleate or dioctyltin diacetate; aluminum tri(ethyl acetoacetate); and compounds of manganese; cobalt or nickel and mineral acids such as trifluoroacetic acid, sulphuric acid, hydrogen chloride, hydrogen bromide, phosphoric acid or perchloric acid.

The catalysts can be added prior to the allophanatization reaction or even prior to the urethanization. They are used in concentrations of 0.001 to 5 wt. %, preferably 0.005 to 1 wt. %. The catalyst may, if practical, be removed from the reaction batch by distillation. However, it may also be useful to stop the catalytic action with suitable catalyst poisons.

The functionality of the resulting products is adjusted by suitable selection of starting components a) and b). The allophanatization reaction is terminated when the desired NCO functionality of the products has been attained. Following the reaction, the excess of unreacted starting component b) is removed, preferably by thin-film distillation, to a residual content in the product of less than 0.5 wt. %, preferably less than 0.2 wt. %.

The products according to the invention are polyisocyanates containing allophanate groups, which have an NCO content from 5 to 17 wt. %, preferably 6 to 15 wt. % and a content of distillable isocyanates of less than 0.5 wt. %, preferably less than 0.2 wt. %. They are viscous to resinous products.

Depending on the viscosity of the products according to the invention, it may be useful to dilute them with inert solvents. Suitable solvents include toluene, xylene, cyclohexane, chlorobenzene, butyl acetate, ethyl acetate, ethylene glycol acetate, pentyl acetate, hexyl acetate, methoxypropyl acetate, tetrahydrofuran, dioxane, acetone, methyl ethyl ketone, solvent naphtha, higher substituted aromatic compounds (such as those commercially available under the trade marks Solvent Naphtha, Solvesso, Shellsol, Isopar, Nappar and Diasol), and mixtures of these solvents.

The products according to the invention are binders for one-component coating compositions, which binders can be cured by the action of atmospheric moisture. However, the products according to the invention are preferably employed as cross-linking agents in two-component polyurethane coating compositions in combination with known polyhydroxyl compounds. In principle it is also possible to block the products according to the invention with blocking agents for isocyanate groups and to use the resulting blocked polyisocyanates in combination with known polyhydroxyl compounds in heat-curable, one-component coating compositions.

Any of the preceding coating compositions may also contain the known additives from coating technology. Examples of these additives include wetting agents, flow-control agents, skinning inhibitors, antifoaming agents, flatting agents such as silica, aluminum silicate and high-boiling waxes, substances for controlling viscosity, pigments, dyes, UV absorbers and stabilizers against thermal or oxidative decomposition.

The coating compositions containing the products according to the invention as binders or binder components can be used for coating any substrates such as wood, plastics, leather, paper, textiles, glass, ceramics, plaster, masonry, metals or concrete. They can be applied by conventional application methods such as spraying, painting, flow coating, pouring, dipping or rolling.

All previously or subsequently stated viscosity data refers to viscosities determined at 23° C. by rotation viscosimetry in accordance with DIN 53 019.

In the following examples all data in "%" refers to weight.

EXAMPLE 1

29.5 g (0.226 mol) of 2-ethylhexanol was placed in a mixing vessel flushed with nitrogen and 19 g (0.113 mol) of HDI was added at 60° C. After a reaction period of approx. 6 hours at a temperature of 95° C., the NCO content of the diurethane formed had fallen to below 0.2%. The allophanatization reaction was then started at 88° C. by the addition of 236 g of TDI (2,4- and 2,6-diisocyanatotoluene in a weight ratio of 80:20) and subsequent catalysis using 43 mg of zinc stearate. After 6 hours the reaction was activated once more with 14 mg of catalyst and stirring was continued until a constant NCO content of 36.2% was obtained. The excess TDI was subsequently separated by thin-film distillation under high vacuum (0.1 to 0.3 mbar) at a temperature of 150° C.

Product data: Yield: 83 g NCO content: 10.8% Viscosity: 75,000 mPa. s/23° C. free TDI content: <0.03%

The $^{13}$C-NMR spectrum shows the characteristic peaks for allophanates but no signals for urethane groups. The low content of free TDI also indicates a simple separation of the monomer during the distillation without decomposition.

EXAMPLE 2

29.5 g (0.226 mol) of 2-ethylhexanol was placed in a mixing vessel flushed with nitrogen and 19 g (0.113 mol) of HDI was added at 60° C. After a reaction period of approx. 6 hours at a temperature of 95° C., the NCO content of the diurethane formed had fallen to below 0.2%. The allophanatization reaction was then started at 88° C. by the addition of 302 g (1.36 mol) of IPDI and subsequent catalysis using 0.35 g of zinc stearate. After 6 hours a constant NCO content of 29.83% was obtained. The excess IPDI was subsequently separated by thin-film distillation under high vacuum (0.1 to 0.3 mbar) at a temperature of 150° C.

Product data: Yield: 90 g NCO content: 9.2% Viscosity: 85,000 mPa.s/23° C. free IPDI content: 0.15%

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a polyisocyanate containing allophanate groups by reacting compound a), which
   i) contains urethane groups, but which is substantially free of hydroxyl groups and isocyanate groups,
   ii) has an average of at least two urethane groups per molecule,
   iii) is prepared by reacting an organic isocyanate a1) with an organic hydroxyl compound a2) and
   iv) has an average molecular weight of at most 2,500,
   with an excess quantity, based on the urethane groups, of a distillable organic polyisocyanate b) to form a polyisocyanate containing allophanate groups and subsequently removing by distillation the unreacted excess of component b) to a residual content of less than 0.5 wt. %, provided that polyisocyanate a1) and polyisocyanate b) are different.

2. The process of claim 1 wherein component a1) comprises a member selected from the group consisting of (i) hexamethylene diisocyanate, (ii) 4,4'-diisocyanatodicyclohexylmethane and mixtures thereof with its 2,4'- and/or 2,2'-isomers, (iii) 1-isocyanato-3,3,5-isocyanatomethylcyclohexane and (iv) 1-methyl-2,4-diisocyanatocyclohexane and mixtures thereof with 1-methyl-2,6-diisocyanatocyclohexane.

3. The process of claim 2 wherein component b) comprises a member selected from the group consisting of i) 2,4-diisocyanatotoluene and mixtures thereof with 2,6-diisocyanatotoluene, (ii) hexamethylene diisocyanate, (iii) 1-isocyanato-3,3,5-trimethyl-5-isocyanatomethylcyclohexane and (iv) 1-methyl-2,4-diisocyanato-cyclohexane and mixtures thereof with 1-methyl-2,6-diisocyanato-cyclohexane.

4. The process of claim 3 wherein a monohydric to hexahydric alcohol having a molecular weight of 32 to 900 or a mixture of these alcohols are used as component a2).

5. The process of claim 1 wherein component b) comprises a member selected from the group consisting of i) 2,4-diisocyanatotoluene and mixtures thereof with 2,6-diisocyanatotoluene, (ii) hexamethylene diisocyanate, (iii) 1-isocyanato-3,3,5-trimethyl-5-isocyanatomethylcyclohexane and (iv) 1-methyl-2,4-diisocyanato-cyclohexane and mixtures thereof with 1-methyl-2,6-diisocyanato-cyclohexane.

6. The process of claim 1 wherein hexamethylene diisocyanate is used as component a1) and (i) 2,4-diisocyanatotoluene and mixtures thereof with 2,6-diisocyanato-toluene and/or (ii) 1-isocyanato-3,3,5-trimethyl-5-isocyanatomethyl-cyclohexane are used as component b).

7. The process of claim 6 wherein a monohydric to hexahydric alcohol having a molecular weight of 32 to 900 or a mixture of these alcohols are used as component a2).

8. The process of claim 1 wherein 4,4'-diisocyanatodicyclohexylmethane and mixtures thereof with its 2,4'- and/or 2,2'-isomers are used as component a1) and hexamethylene diisocyanate is used as component b).

9. The process of claim 8 wherein a monohydric to hexahydric alcohol having a molecular weight of 32 to 900 or a mixture of these alcohols are used as component a2).

10. The process of claim 1 wherein a monohydric to hexahydric alcohol having a molecular weight of 32 to 900 or a mixture of these alcohols are used as component a2).

11. A polyisocyanate containing allophanate groups which is prepared by reacting a compound a), which i) contains urethane groups, but which is substantially free of hydroxyl groups and isocyanate groups, ii) has an average of at least two urethane groups per molecule, iii) is prepared by reacting an organic isocyanate a1) with an organic hydroxyl compound a2) and iv) has an average molecular weight of at most 2,500, with an excess quantity, based on the urethane groups, of a distillable organic polyisocyanate b) to form a polyisocyanate containing allophanate groups and subsequently removing by distillation the unreacted excess of component b) to a residual content of less than 0.5 wt. %, provided that polyisocyanate a1) and polyisocyanate b) are different.

12. The polyisocyanate of claim 11 wherein component a1) comprises a member selected from the group consisting of (i) hexamethylene diisocyanate, (ii) 4,4'-diisocyanato-dicyclohexylmethane and mixtures thereof with its 2,4'- and/or 2,2'-isomers, (iii) 1-isocyanato3,3,5-isocyanatomethylcyclohexane and (iv) 1-methyl-2,4-diisocyanatocyclohexane and mixtures thereof with 1-methyl-2,6-diisocyanatocyclohexane.

13. The polyisocyanate of claim 12 wherein component b) comprises a member selected from the group consisting of i) 2,4-diisocyanatotoluene and mixtures thereof with 2,6-diisocyanatotoluene, (ii) hexamethylene diisocyanate, (iii) 1-isocyanato-3,3,5-trimethyl-5-isocyanatomethylcyclohexane and (iv) 1-methyl-2,4-diisocyanatocyclohexane and mixtures thereof with 1-methyl-2,6-diisocyanatocyclohexane.

14. The polyisocyanate of claim 13 wherein a monohydric to hexahydric alcohol having a molecular weight of 32 to 900 or a mixture of these alcohols are used as component a2).

15. The polyisocyanate of claim 11 wherein component b) comprises a member selected from the group consisting of i) 2,4-diisocyanato-toluene and mixtures thereof with 2,6-diisocyanatotoluene, (ii) hexamethylene diisocyanate, (iii) 1-isocyanato-3,3,5-trimethyl-5-isocyanatomethylcyclohexane and (iv) 1-methyl-2,4-diisocyanatocyclohexane and mixtures thereof with 1-methyl-2,6-diisocyanatocyclohexane.

16. The polyisocyanate of claim 11 wherein hexamethylene diisocyanate is used as component a1) and (i) 2,4-diisocyanatotoluene and mixtures thereof with 2,6-diisocyanato-toluene and/or (ii) 1-isocyanato-3,3,5-trimethyl-5-isocyanatomethyl-cyclohexane are used as component b).

17. The polyisocyanate of claim 16 wherein a monohydric to hexahydric alcohol having a molecular weight of 32 to 900 or a mixture of these alcohols are used as component a2).

18. The polyisocyanate of claim 11 wherein 4,4'-diisocyanatodicyclohexylmethane and mixtures thereof with its 2,4'- and/or 2,2'-isomers are used as component a1) and hexamethylene diisocyanate is used as component b).

19. The polyisocyanate of claim 18 wherein a monohydric to hexahydric alcohol having a molecular weight of 32 to 900 or a mixture of these alcohols are used as component a2).

20. The polyisocyanate of claim 11 wherein a monohydric to hexahydric alcohol having a molecular weight of 32 to 900 or a mixture of these alcohols are used as component a2).

21. A coating composition containing the polyisocyanates of claim 11 as the binder or a binder component.

* * * * *